US011202673B1

(12) United States Patent
Jacobowitz et al.

(10) Patent No.: US 11,202,673 B1
(45) Date of Patent: Dec. 21, 2021

(54) POLARIZED ELECTRIC FIELD SYSTEM FOR WHOLE-BODY COVID-19 THERAPY

(71) Applicants: Lawrence Jacobowitz, Boynton Beach, FL (US); Alan M. Victor, Raleigh, NC (US)

(72) Inventors: Lawrence Jacobowitz, Boynton Beach, FL (US); Alan M. Victor, Raleigh, NC (US)

(*) Notice: Subject to any disclaimer, the term of this patent is extended or adjusted under 35 U.S.C. 154(b) by 0 days.

(21) Appl. No.: 17/242,514

(22) Filed: Apr. 28, 2021

(51) Int. Cl.
*A61B 18/18* (2006.01)
*A61B 18/00* (2006.01)
*A61B 17/00* (2006.01)

(52) U.S. Cl.
CPC ........... *A61B 18/1815* (2013.01); *A61B 2017/00159* (2013.01); *A61B 2017/00725* (2013.01);
(Continued)

(58) Field of Classification Search
CPC ............ A61B 18/18; A61B 18/1815; A61B 2018/0016; A61B 2018/00541; A61B 2018/00613; A61B 2018/00636; A61B 2018/00642; A61B 2018/00988; A61B 2018/1823; A61B 2018/1838; A61B 2018/00779; A61B 2018/00678; A61B 2018/0072; A61B 2018/00767; A61N 5/02; A61N 5/025; A61N 5/1001;
(Continued)

(56) References Cited

U.S. PATENT DOCUMENTS

| 6,589,786 B1 | 7/2003 | Mangano et al. |
| 9,585,408 B2 | 3/2017 | Hyde et al. |

(Continued)

OTHER PUBLICATIONS

Polozov et al. Cylindrical Phased Dipoles Array For Hyperthermia of Deep-Situated Tumors, Proceedings of RUPAC2012, https://www.researchgate.net/publication/265274872, Saint-Petersburg, Sep. 2012, pp. 521-523.

(Continued)

*Primary Examiner* — Thomas A Giuliani
(74) *Attorney, Agent, or Firm* — Scully, Scott, Murphy & Presser, PC

(57) ABSTRACT

A non-invasive electrodynamic radiative electroporation system and method for safe in vivo delivery of specific radiant energy to physiologically inaccessible sites for selective destruction of biomolecular function of virions, particularly Covid-19 and its variants. The system and method applies a computer or like controller to generate, modulate, direct and deliver applied external electric fields from plural antennas to target tissues in the full respiratory tract, including lung microstructures, cardiovascular tissues and neuron networks. Electric fields exceeding a critical threshold-value interact with the virus lipid bilayer membranes, intra-membrane organelles, mRNA, and biomolecular scaffold assemblies, to destroy virion function through irreversible electroporation and electropermeabilization. Polarized electric fields are generated to provide force vectors in optimal dynamic angular distribution to the virion membrane surface and modulated within time-scales short compared to thermal transport characteristic times to effect the electroporation as an adiabatic process that preempts Joule heating of normal tissues.

20 Claims, 14 Drawing Sheets

(52) U.S. Cl.
CPC ........... *A61B 2018/0016* (2013.01); *A61B 2018/0072* (2013.01); *A61B 2018/00613* (2013.01); *A61B 2018/00642* (2013.01); *A61B 2018/00678* (2013.01); *A61B 2018/00767* (2013.01); *A61B 2018/00779* (2013.01); *A61B 2018/1823* (2013.01); *A61B 2018/1838* (2013.01)

(58) Field of Classification Search
CPC ...... A61N 2005/0637; A61N 2005/027; A61N 2005/0638
USPC ........... 606/33, 34, 41, 42; 607/98–101, 115
See application file for complete search history.

(56) References Cited

U.S. PATENT DOCUMENTS

| | | | |
|---|---|---|---|
| 10,010,718 | B2 | 7/2018 | Basiony |
| 10,551,449 | B2 | 2/2020 | Makarov et al. |
| 2005/0140542 | A1* | 6/2005 | Ikeda ............... G01S 13/0209 342/118 |
| 2013/0261683 | A1* | 10/2013 | Soikum ............... C12N 13/00 607/2 |
| 2018/0168729 | A1* | 6/2018 | Pratten ............... A61B 5/01 |
| 2020/0197687 | A1 | 6/2020 | Asirvatham et al. |
| 2020/0305265 | A1 | 9/2020 | Eckert et al. |

OTHER PUBLICATIONS

Hjouj et al. "MRI Study on Reversible and Irreversible Electroporation Induced Blood Brain Barrier Disruption," PLOS ONE; https://doi.org/10.1371/journal.pone.0042817. Aug. 10, 2012. vol. 7: 8; 9 pages.

Anderson, M. "UV Light Might Keep the World Safe From the Coronavirus—and Whatever Comes Next." IEEE Spectrum;https://spectrum.ieee.org/biomedical/devices/uv-light-might-keep-the-worid-safe-from-the-coronavirusand-whatever-comes-next. Sep. 28, 2020. 8 pages.

Du Toit, A. "Coronavirus Replication Factories," Nature Reviews Microbiology. Aug. 2020. vol. 18:411. 1 page.

Wolff et al. "A Molecular Pore Spans the Double Membrane of the Coronavirus Replication Organelle," Science 369, Sep. 11, 2020. pp. 1395-1398.

Wolff et al, "Double-Membrane Vesicles as Platforms for Viral Replication," Trends in Microbiology; https://doi.org/10.1016/j.tim.2020.05.009, Dec. 2020. vol. 28: 12. pp. 1022-1033.

Schoenbach et al. "The Effect of Pulsed Electrical Fields on Biological Cells," IEEE Conference Paper, Jan. 1997. 6 Pages.

Snijder et al. "A unifying structural and functional model of the coronavirus replication organelle:Tracking down RNA synthesis," PLOS Biology; https://doi.org/10.1371/journal.pbio.3000715. Jun. 8, 2020. 25 pages.

Pereira et al. "Synthesis of Antennas for Field and Polarization Control," Journal of Electromagnetic Analysis and Applications; https://doi.org/10.4236/jemaa.2017.97009 Jul. 19, 2017. pp. 97-112.

Napotnik et al. "Effects of high voltage nanosecond electric pulses on eukaryotic cells (in vitro): A systematic review," Accepted Feb. 23, 2017.110,1-al. pp. 1-12.

Morshed et al. "Electrical Lysis: Dynamics Revisited and Advances in On-chip Operation," Critical Reviews in Biomedical Engineering. 2013. pp. 37-50. vol. 41 (1).

Morshed et al. "Deriving an Electric Circuit Equivalent Model of Cell Membrane Pores in Electroporation." Biophysical Reviews and Letters; DOI: 10.1142/S1793048012500099. Accepted Nov. 28, 2012 and Published Jan. 10, 2013. pp. 1-13. vol. 7, No. 4.

Delemotte et al. "Molecular Dynamic Simulations of Lipid Membrane Electroporation," The Journal of Membrane Biology; DOI:10 1007/S00232-012-9434-6. May 2012 14 pages.

Bockmann et al, "Kinetic Statistics and Energetics of Lipid Membrane Electroporation Studies by Molecular Dynamics Simulations," Biophysical J. vol. 95 (Aug. 2008), 1837-1850.

Ringel-Scaia et al, "High-Frequency irreversible electroporation is an effective tumor ablation strategy that induces immunologic cell death and promotes systemic anti-tumor immunity." EBioMedicine/The Lancet, 44,(2019), pp. 112-125.

Sengel et al, "Measuring the potential energy barrier to lipid bilayer electroporation," Phil. Trans.R.Soc.B 372: 20160227; http://dx.doi.org/10.1098/rstb.2016 0227. (2017). 7 pages.

Hart et al, "The Application of Electric Fields in Biology and Medicine," IntechOpen 71683, Ch8, Dec. 20, 2017 pp. 162-186.

Tadesse, The Electromagnetic Simulation of Birdcage Coils for MRI Based On Finite Element Method, M.S. thesis, Youngstown U., Fall 2016,. 67 pages.

Connor et al, "Electromagnetic Absorption by the Human Body from 1 to 15 GHz" A thesis submitted for the Ph.D. degree The University of York Department of Electronics. Aug. 2013. 170 pages.

King, "The Electric Field Induced in the Human Body When Exposed to Electromagnetic Fields at 1-30 MHz on Shipboard," IEEE Trans. on Biomedical Engineering vol. 46, No. 6 (Jun. 1999). 5 Pages.

Catellani et al, "Permeabilizing Phospholipid Bilayers With Non-normal Electric Fields," J. Membrane Biology 1432-1434, Apr. 2018. 8 pages.

Tang et al. "Terahertz Electric Field-Induced Membrane Electroporation by Molecular Dynamics Simulations," The J. of Membrane Biology 251(5-6), Nov. 2018. 13 pages.

Morfill et al. Cold Plasma Against the Coronavirus, Max-Planck Gesellschaft, Science Magazine, Jun. 11, 2020. 3 Pages.

Chen et al., "Cold atmospheric plasma for COVID-19," Department of Mechanical and Aerospace Engineering University of California; Apr. 8, 2020, pp. 1-7, doi:10.20944/preprints202004.0126.v1.

Pavlin et al,, "Electroporation of Planar Lipid Bilayers and Membranes," Advances in Planar Lipid Bilayers and Liposomes, 2018, pp. 165-213, vol. 6, Ch7, Elsevier Pub.

Kolb et al. "Sub-Nanosecond Electrical Pulses for Medical Therapies and Imaging," Proceedings of the Fourth European Conference on Antennas and Propagation, Apr. 12-16, 2010, pp. 1-5.

\* cited by examiner

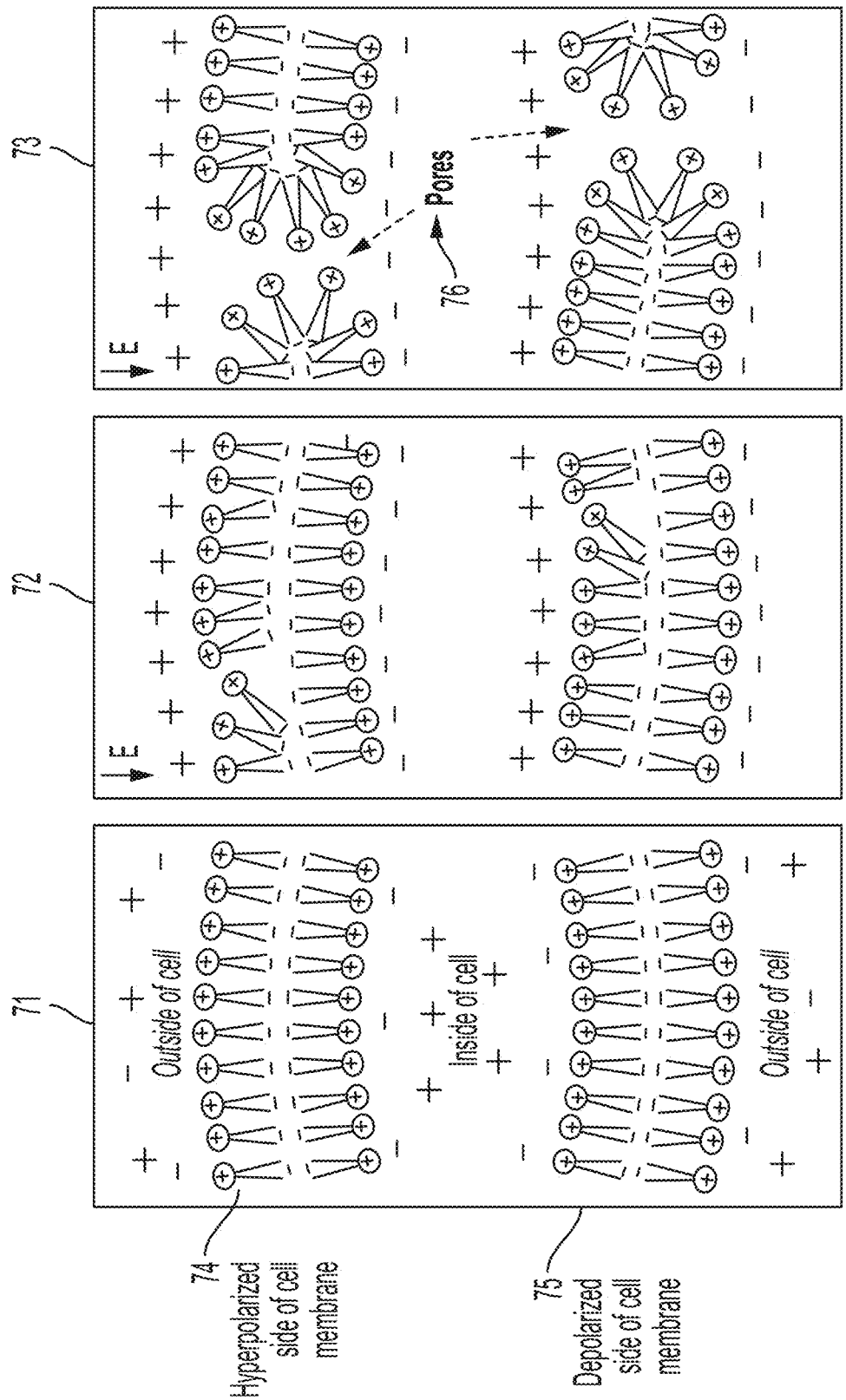

POLARIZED ELECTRIC FIELD SYSTEM FOR WHOLE-BODY COVID-19 THERAPY

FIELD

The present application generally relates to systems and methods for pathogen decomposition, and in particular, to non-invasive electronic therapy systems and methods to selectively destroy pathogens on the surface receptors of human tissues.

BACKGROUND

Current solutions for in vivo applications of direct-current (DC) or radio frequency (RF) electric fields, cold atmospheric plasma (CAP), or ultraviolet light (UV-C), to destroy virions, bacteria, or carcinomic tissues, have been limited by physiological inaccessibility, device dimensional constraints, and incomplete biophysical data on safe levels for in vivo electromagnetic radiation.

Moreover, prior art solutions are based on invasive injected polarized needle electrode electroporation.

The onset of the novel corona virus (Covid-19) global pandemic has driven a spate of recent relevant publications providing new laboratory data and has exhibited strong demands for safe and effective therapeutics.

For example, recent publications have elicited the structure and replication process of the Coronavirus. It has been shown that the virus is comprised of a two layer lipid membrane, commonly referred to as a bilayer membrane. Viral RNA is embedded as a strand within the bilayer membrane and a complex process of genetically coded information allows hijacking infected host cells for viral replication by budding via the host cell membrane. The recently identified replication organelle, RO, of the virus has been associated with a vesicle in the virion membrane and has become a target for therapeutic drug research.

Current prior art approaches that use fiber-optic endoscopes to access to receptor bound Coronavirus is limited by anatomical or physiological structures.

Further, there exists current biophysics literature addressing the fundamental dynamic laws explaining the process of electroporation. In brief, ionic channels and nanopores or micropores have been identified and distinctions from pure dielectric breakdown theory have appeared in recent publications. The dominant short-range mechanism is the Coulomb force of the external applied electric field exerted on the electric dipoles comprising the sheet of hydrophilic, polar phospholipid head groups comprising the membrane. A collective resultant tensile force greater than the surface tension of the electric dipole ensemble effects membrane rupture. This collective resultant force is the Maxwell stress tensor. Ancillary transmembrane potential increases assist the process.

SUMMARY OF THE INVENTION

The present invention is a computer-implemented system and method for selective destruction of target pathogens based on non-invasive external radiative electroporation, and in particular, a system and method for creating specific controlled conditions based on external applied electric fields for in vivo destruction of virions such as Coronaviruses, including COVID-19 and variants, without damage to normal tissues.

In an embodiment, the system and method delivers specific polarized radiant energy to target tissues to achieve selective destruction of targets in vivo, the targets including but not limited to: pathogens, cancer tumors, cardiac tissues, nervous system structures, and, biological units.

The system and methods for selective destruction of target pathogens achieves disruption of the virion reproductive apparatus through radiative electroporation of the virus membrane. Sterilization is defined in this context.

In one embodiment, the present invention is directed to a computer-implemented system and method for generating, modulating, directing and delivering non-ionizing external electric fields from antennas to in vivo target tissues in the full respiratory tract, including lung microstructures, cardiovascular tissues and neuron networks, for irreversible electroporation (IRE) of coronavirus.

The computer-implemented system comprises sensor-based feedback loop electronic circuits configured to limit specific absorption rates, SAR, for control of patient exposure to not exceed established regulatory requirements for safe levels of electromagnetic radiation.

In one embodiment, the computer-implemented system comprises electronic circuits provided to generate and modulate or pulse the electric field in order to enable higher peak power levels to improve whole body penetrability. Sensor-based feedback control loops are provided to enable computer control of operating parameters. Electric field generation using adaptive antenna arrays accommodate variable treatment needs such as patient positioning, modalities, dosages, and monitoring.

In one aspect, there is provided a non-invasive radiative electroporation apparatus for in vivo selective destruction or sterilization of biological targets. The system comprises: a radio frequency signal generator generating polarized radiant energy signals at one or more radio frequency antennas, each antenna located proximate the patient and having a geometry for delivering specific polarized radiant energy at a selected field intensity level to tissues of the patient having the biological targets; electronic circuitry configured to modulate the polarized radiant energy signals according to a configured waveform and exposure time for delivery of the polarized radiant energy signals to the biological targets; a patient support table adapted for adjusting positioning of a patient relative to the radiant energy source(s); one or more processors coupled to a memory storage for storing a computer readable instructions, at least one processor adapted to run the computer-readable instructions to configure the at least one processor to: configure the electronic circuit to adjust operating radiant energy parameters for controlling the waveform and exposure time; and a plurality of electric field sensors disposed relative to the patient support table for sensing polarized radiated energy signals delivered to the patient tissues and generating associated feedback signals, the at least one processor using the feedback signals to adjust the operating radiant energy parameters for constraining the delivered polarized radiant energy signals to within a specified electrical field intensity level safety limit.

In a further aspect, there is provided a method of non-invasive radiative electroporation for in vivo selective destruction or sterilization of biological targets within a patient. The method comprises: generating, using a radio frequency signal generator, polarized radiant energy signals at one or more radio frequency antennas, each antenna located proximate the patient and having a geometry for delivering specific polarized radiant energy at a selected field intensity level to tissues of the patient having the biological targets; modulating the polarized radiant energy signals according to a configured waveform and exposure time for delivery of the polarized radiant energy signals to the biological targets; receiving, at at least one processor, programmed instructions for configuring the at least one processor to program an electronic circuit to adjust operating radiant energy parameters for controlling the waveform and exposure time; and sensing, using a plurality of electric field sensors disposed relative to the patient, polarized radiated energy signals delivered to the patient tissues and generating associated feedback signals, the at least one processor using the feedback signals to adjust the operating radiant energy parameters for constraining the delivered polarized radiant energy signals to within a specified electrical field intensity level safety limit.

BRIEF DESCRIPTION OF THE DRAWINGS

FIGS. 4A-4C depict the coronavirus phospholipid bilayer membrane construction comprised of electric dipoles and their resulting interaction when subject to various electrical fields in an example embodiment;

DETAILED DESCRIPTION OF THE INVENTION

Figure 1B:
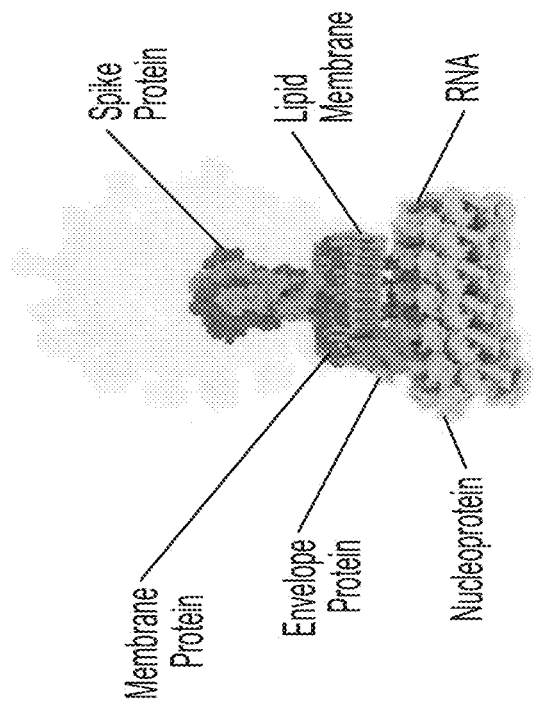
FIG. 1(b) is a cross-sectional view of the lipid bilayer membrane partitioning the intracellular nucleoprotein and mRNA from the extracellular spike protein.
Figure 1A:
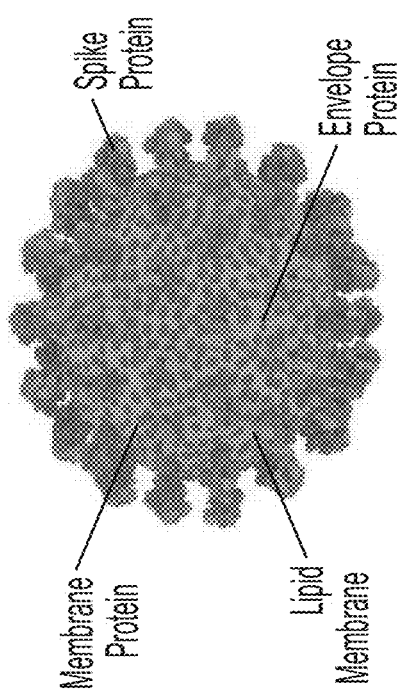
FIG. 1(a) exhibits the covid-19 Coronavirus cellular structures with spherical morphology, spike protein, and, lipid membrane envelope.
Figure 2:
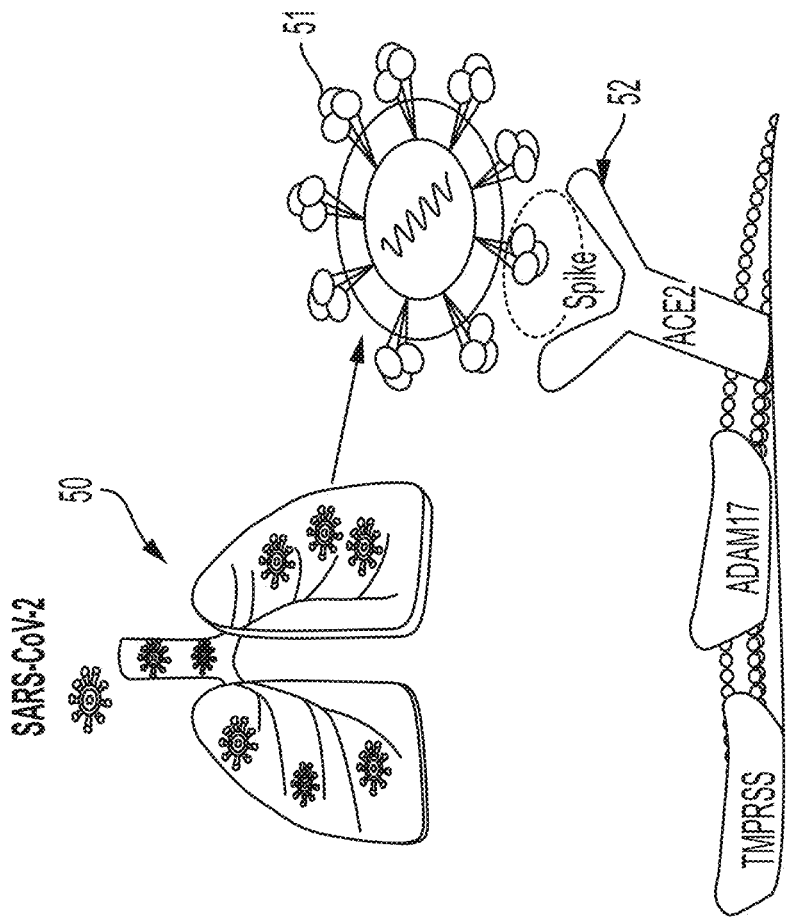
FIG. 2 depicts the anatomical loci of infection sites in the trachea and lungs along with the spike protein attachment to the Ace 2 receptor binding site residing on host tissue surfaces

FIG. 1A depicts the physical structure of the Coronavirus showing a spherical morphology with spike proteins covering the surface comprised of a lipid membrane, membrane protein, and envelope protein. The virus lipid membrane is a bilayer lipid membrane surrounding an intracellular volume. In the intracellular volume shown in FIG. 1B, there resides nucleoprotein and RNA. Recent research has identified this RNA to be central to production of viral progenitors via a replication organelle. The ingress pathway of Coronavirus is exhibited in FIG. 2 illustrating the nasopharyngeal 50 to trachea to lungs to alveoli sacs whose tissues are lined with ACE 2 (angiotensin converting enzyme, type 2) receptors represented as "Y" shapes 52. As depicted in FIG. 2, the Covid protein spike 51 binds to the ACE2 receptor 52 attached to the host cell membrane.

Figure 3:
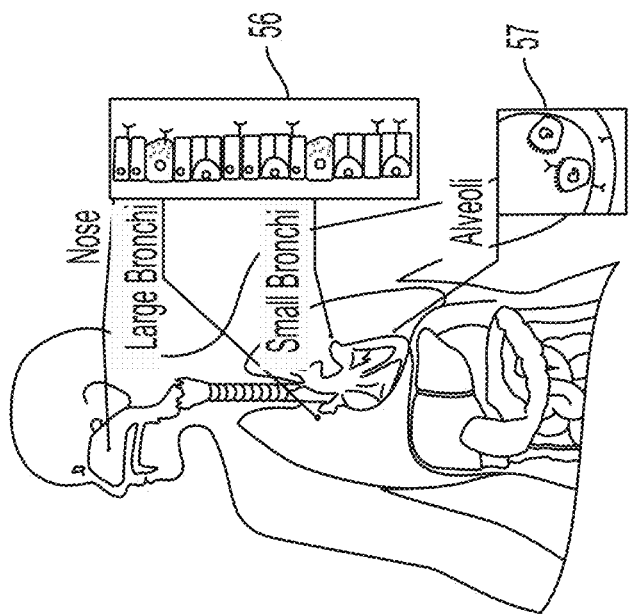
FIG. 3 represents the human body target organs of a patient undergoing antenna-based radiative electroporation therapy in an example embodiment.

FIG. 3 expands the anatomical view to the whole body systems, including the heart, vascular system, and, nervous system (not shown). As depicted in FIG. 3, the Covid protein spike binds to the ACE2 receptor attached to the host cell membrane at 56 and 57.

In an embodiment, an apparatus runs methods configuring a plurality of radiating antennae to generate and apply electrical field(s) that enable the destruction of the virus bilayer lipid membrane by introducing the electric field(s) to interact with the molecular chains or head groups which are electric dipoles comprising the virus membrane. The generated electric field interacts with the electric dipoles through the Coulomb force which is the product of the charge of the dipole with the applied electric field. A torque is produced which opens pores in the bilayer lipid membrane, assisted by an increase in the transmembrane electric potential, and produces irreversible electroporation (IRE) under the specified conditions provided by the apparatus. Hence, the electroporation process annihilates the replication organelle, the mRNA, and destroys the virion membrane function.

FIGS. 4A-4C depict the coronavirus phospholipid bilayer membrane construction comprised of electric dipoles in upper layer 74 and lower layer 75 and their resulting interaction when subject to various electrical fields. In FIG. 4A, bilayer lipid membrane states are shown for no electric field applied 71 resulting in a stable bilayer membrane state; FIG. 4B shows bilayer lipid membrane states in the presence of an electric field 72 resulting in a reorientation of the phospholipids; and FIG. 4C shows bilayer lipid membrane states under sustained electric field 73 resulting in the formation of hydrophilic pores 76.

For a lipid membrane thickness of the order of 5 nm, an electric field intensity of the order of 5 mV can produce electrical lysis of the virion lipid membrane. Noting that the corona virus is typically of the order of 90 nm-140 nm in diameter and somatic cells of the order of or greater than 10 microns, about 100 to 1,000 times larger, the electric field power-density is readily matched to provide the required electric field for electroporation or electropermeation destruction of Covid-19 viruses without harm to surrounding somatic cell DNA.

In an embodiment, the apparatus configures antenna to apply signals, e.g., square-wave pulses of width of the order of psec to nsec with low duty-cycles to achieve electroporation adiabatically (without thermal transport effects), thereby obviating the Joule heat to tissues which the SAR standards are predicated on. To obviate restoring forces closing pores, unipolar pulses may be employed advantageously in a pulse train within an optimized duty-cycle.

Corrections for dielectric parameters of human tissues are included in the application of electric fields. Variations in electric field intensities and polarizations are achieved through variations in design parameters and are computer controlled well below human tissue damage thresholds. Notably, patient size, weight, density, gender, and related factors, are SAR variables accounted for in computer parameter settings. As noted, radiative electroporation at time-scales of picoseconds (ps) to nanoseconds (ns) are adiabatic, obviating Joule heating of tissues.

In an embodiment, the time-scale for the electroporation interaction is of the order of hundreds of picoseconds to one nanosecond, and, may be accomplished in one or more ultrashort pulses. The apparatus configures the antennae to apply radiative electroporation to accomplish in vivo destruction of the fundamental biomolecular structure of the virion membrane and at the psec or nsec time-scale, Joule heating is negligible.

The Chamber

Figure 5:
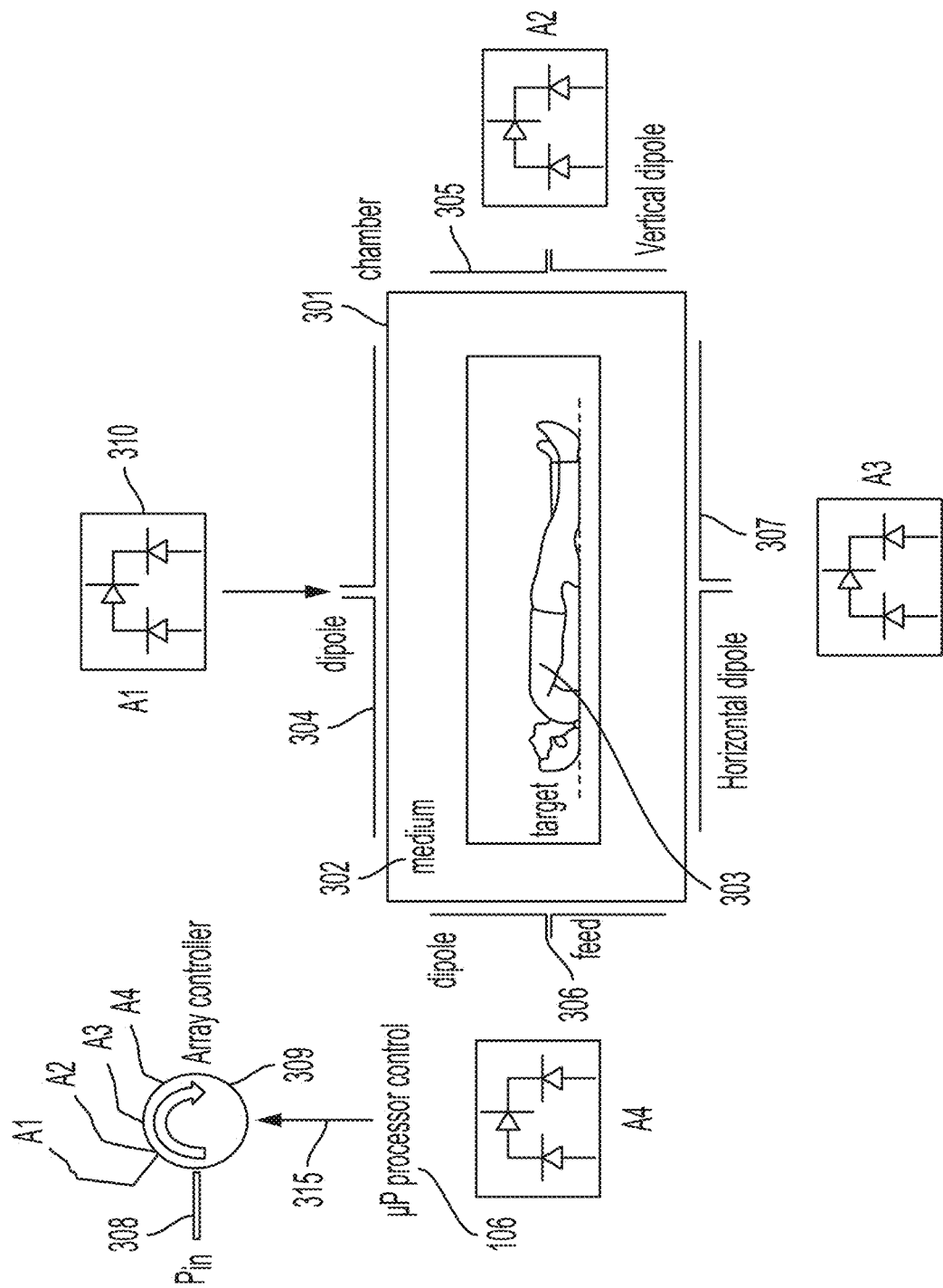
FIG. 5 shows the apparatus for delivering an external applied electric field for in vivo whole body sterilization of pathogens, such as Covid-19 in an example embodiment.
Figure 6A:
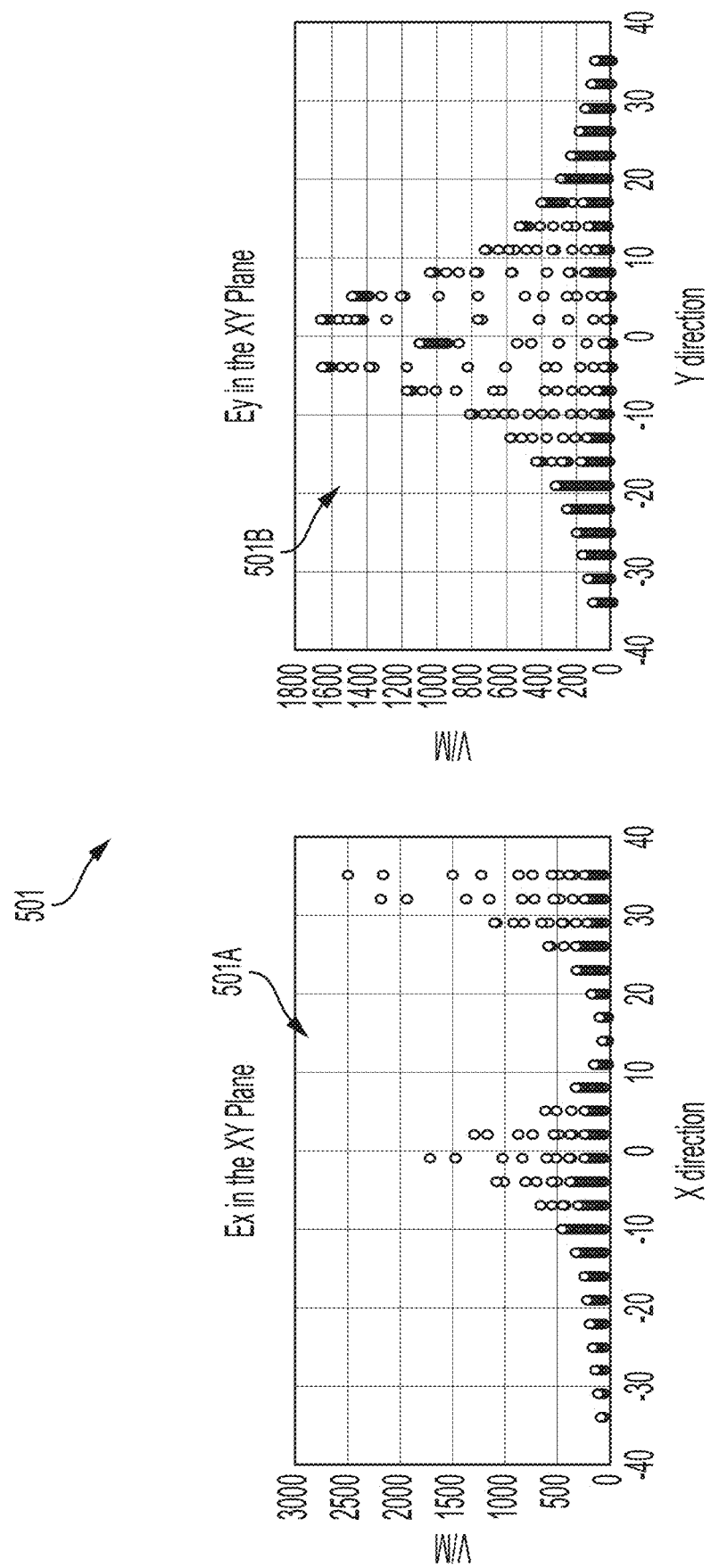
FIG. 6A is an illustration of the x-axis and y-axis electric field components of the electric field spatial distribution and FIG. 6B is an illustration of the z-axis electric field components of the electric field spatial distribution in a coordinate frame relative to a target patient undergoing antenna-based radiative electroporation therapy.
Figure 6B:
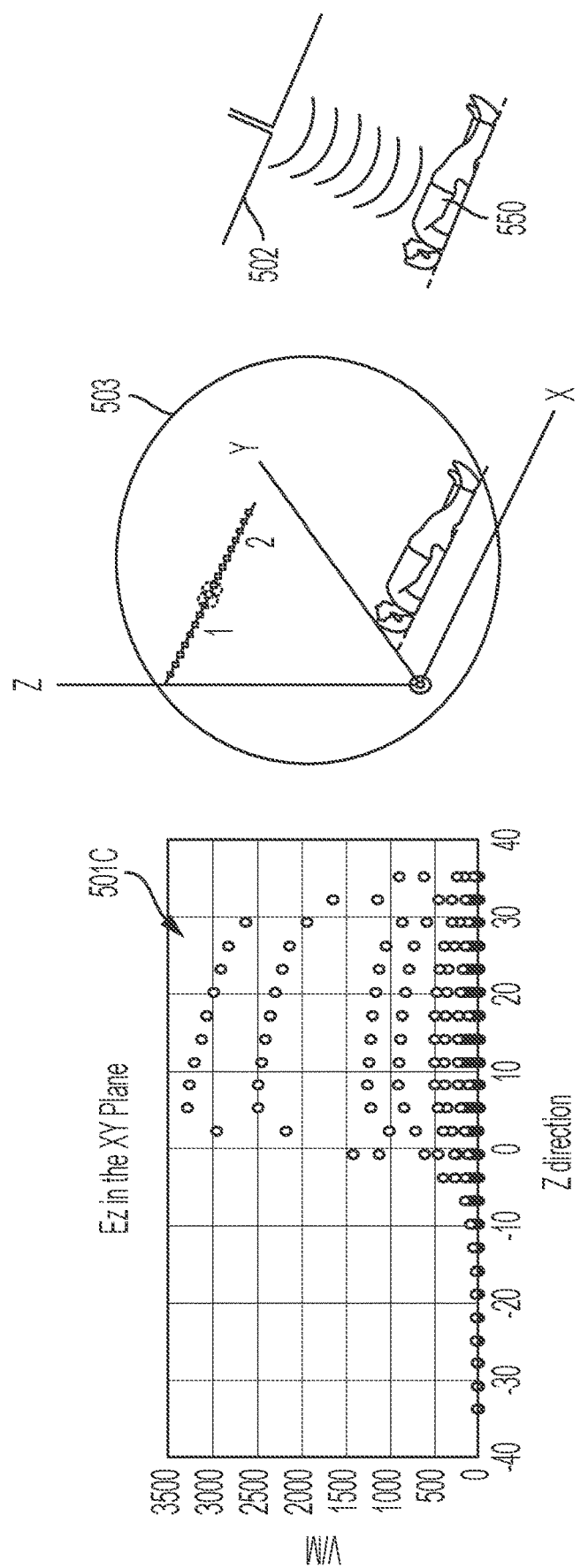

FIG. 5 depicts one embodiment of a chamber 301 within which a patient 303 is exposed to radiating antennas, e.g., dipole antenna 304, vertical dipole antenna 305, an antenna feed 306, a horizontal dipole antenna 307 directing respective electric fields towards the patient 303. The chamber 301 is transparent to the operating frequency. In an embodiment, the operating frequency is about 40.60 MHz. Dipole antennas are bent as required to maintain the form factor of the chamber. Dipoles are laid in horizontal 304 and/or vertical 305. All feeds 306 are coaxial or open wire feed as required to permit impedance matching to the E field generation system and high efficiency. In an embodiment, the system includes a main excitation feed 306 receiving input signal P. 308 that is fed to array controller 309 for generating individual signals A1, A2, A3, A4. The array controller responds to input signals 315 received from a microprocessor or like control device to synchronize generation of respective power output signals A1, A2, A3, A4 from array controller 309. Each signal A1, A2, A3, A4 is fed to respective dipole antennas 304-307 and is received at respective constant impedance matching PiN diode network attenuators and phase shifter 310.

In an embodiment, a medium 302 can be introduced surrounding the walls of the chamber such as a layer of material having a dielectric constant different than air to assist in E field distribution. For example, a water bladder medium may be attached to the inner walls of the chamber 301.

In a further embodiment, a scanning system (not shown) is implemented to scan the dipole antenna or array of dipole antennas in a lateral or longitudinal direction across a stationary patient, or scan via a rotation, to provide for whole body coverage of the patient. In an embodiment, the dipole antenna is comprised of discrete segments or sections for adaptive radiation pattern generation and control. The dipole antenna is further rotatable to generate controlled emission patterns and polarization states of the electric field.

The E Field Generator

Laboratory studies have measured the electric field threshold for virion membrane irreversible electroporation to be on the order of 0.1 MV/m to 0.15 MV/m. For electroporation and electropermeation of virion phospholipid bilayer membranes in vivo, an external electric field of specific critical electric field strength must be delivered to target tissue surfaces where virions attach to ACE 2 and other receptors. Unlike the problem of MRI head imaging with significant bone SAR, specific absorption rate, the thoracic and nasopharyngeal regions pose lower SAR values to body-penetrating electric fields at lower rf frequencies, suitable for inducing nanoscale defects resulting in virion lipid membrane destruction. Unlike MRI apparatus, strong magnetic fields are not required.

In an embodiment, the system generates electric field magnitudes for electroporation that spans an interval greater than the electroporation threshold and less than the regulatory safety standard SAR values. Characteristic time-constants to achieve electroporation begin below 1 nsec. As shown in FIGS. 4B, 4C electric field vectors operate on the virus membrane surface via the Coulomb force on the positive hydrophylic charges of polymers comprising a matrix of electric dipoles. The collective resultant forces comprise the Maxwell stress tensor. The rapid interaction of the electric field with these electric dipoles is accomplished without Joule heating or heat transfer, such that radiative electroporation is adiabatic. Advantageously, SAR, specific absorption rate, is therefore negligible.

Figure 10:
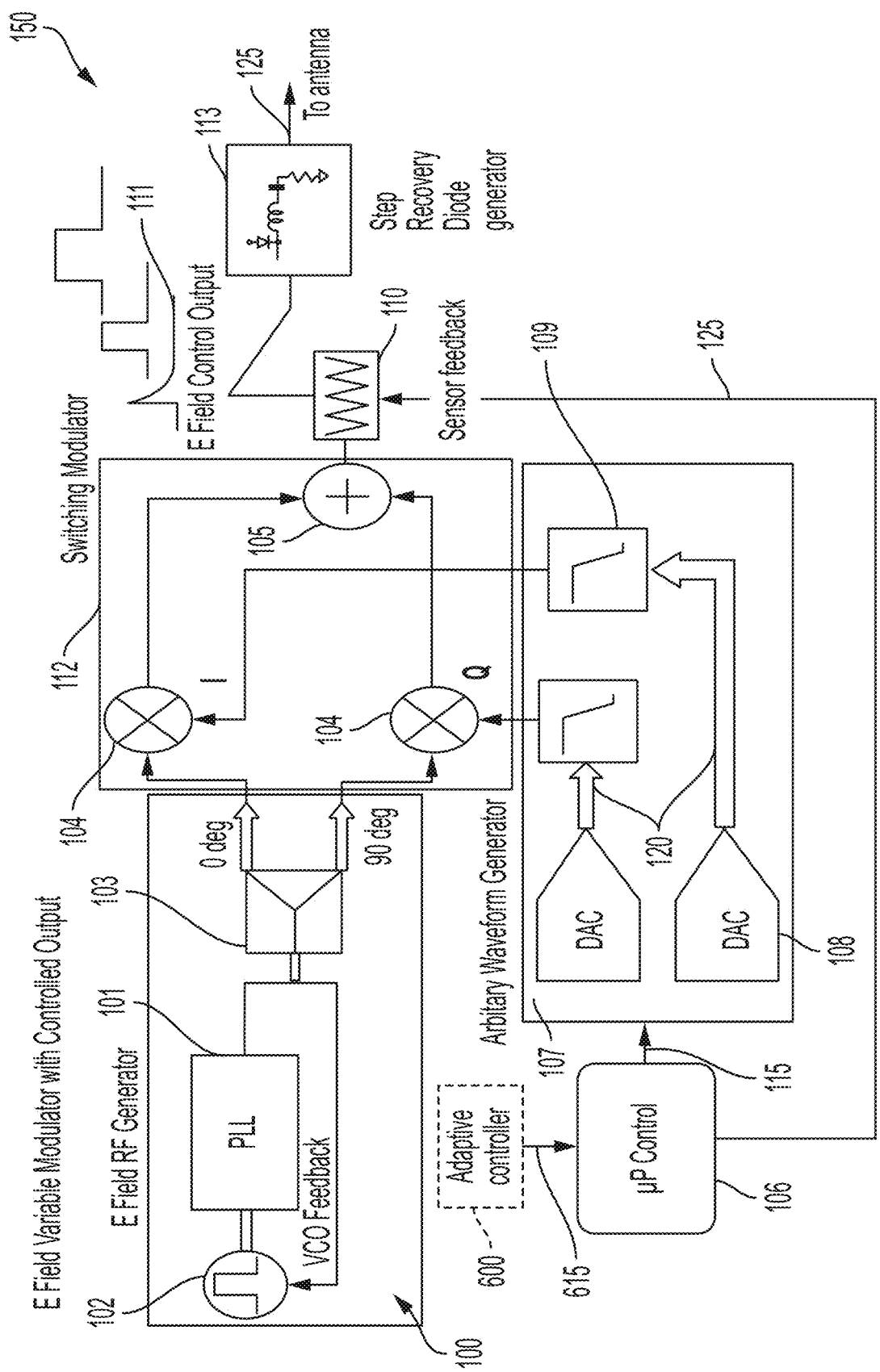
FIG. 10 shows the functional circuit structure of electric field generation and modulation via antennas suitable for in vivo delivery of controlled electric fields for radiative electroporation in an example embodiment.
Figure 11:
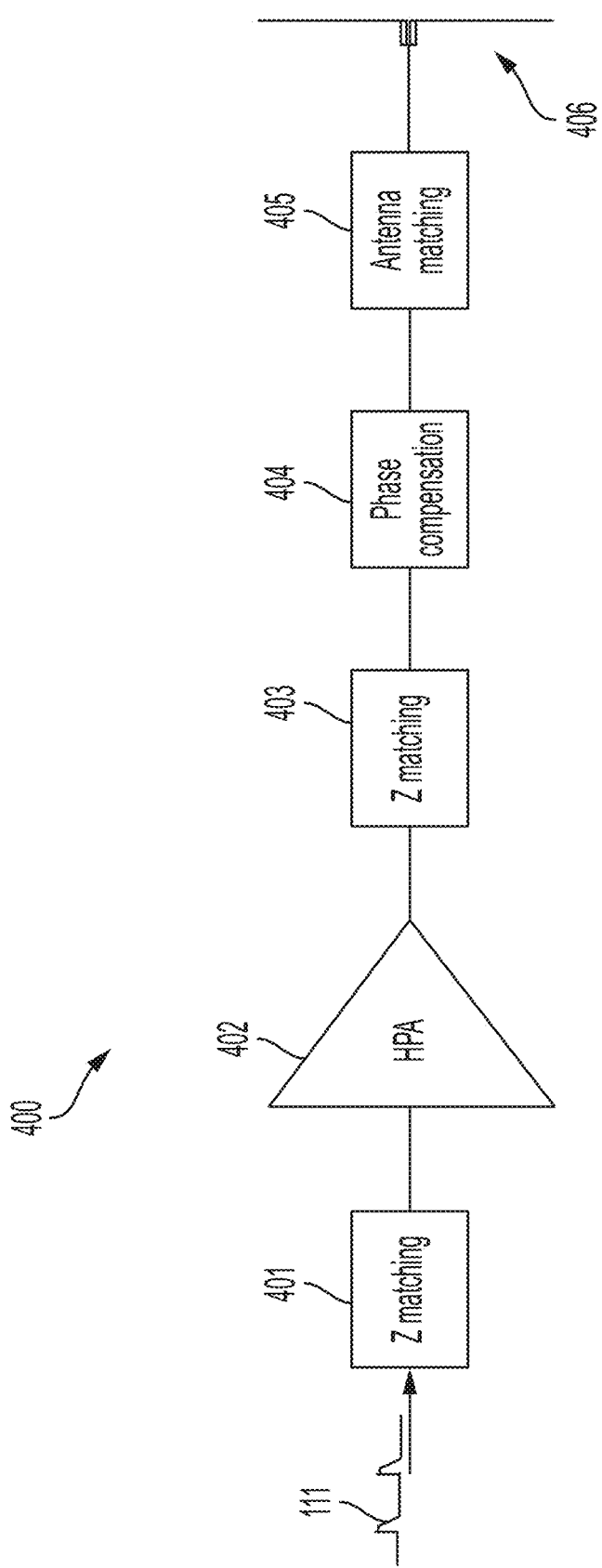
FIG. 11 exhibits the chamber antenna drives, feeds, phase compensation, impedance matching network and power amplifier configuration in an example embodiment.

FIG. 10 shows a radio frequency (RF) generation system 150 for generating polarized radiation in an embodiment of the invention. In particular, the RF generation system 100 applies an arbitrary waveform current or voltage excitation to a pulse shaping network. The system targets a unipolar pulse waveform that maintains an appropriate wave front rise time, fall time, pulse width and repetition rate conducive to virus destruction. The E field variable modulator core includes an E field RF generator 100 which consists of a digital phase lock loop, a PLL 101 and digital controlled oscillator 102, e.g., a voltage controlled oscillator (VCO) which provides for a stable signal generation. The generator output is split into a pair of quadrature signals (i.e., 0° and 90°) via a 90° quadrature phase splitter 103 and delivers these signals to switching modulator 112. The switching modulator 112 contains In phase, I, and Quadrature phase, Q, switching mixers 104 whose outputs are summed in summation element 105. The I and Q switching mixers receive their inputs from an arbitrary waveform generator 107 serving as a modulator. This modulator provides a programmable waveform under control of a microprocessor or microcontroller 106. Microcontroller 106 issues digital command signals 115 suitable for virus membrane electroporation and which are processed and subsequently delivered as an appropriate intensity E field with correct polarization. Programming of a pulsed signal signature is provided by a set of digital to analogue converters (DAC) 108 receiving command signals 115. The analog signal outputs 120 of the DACs 108 are suitably shaped by filters 109, e.g., low pass filters, which will work with other compensation circuits to assist in maintaining the proper pulsed signature signal when delivered to the antenna system. The summer output 105 which now contains pulse modulated signal is controlled as a current or a voltage of proper level thru a leveler and voltage controlled attenuator element 110 and is received at a further pulse shaping network 113 which utilizes a step recovery diode network. The pulse shaping network 113 provides a fast sub nanosecond pulse shape which can take on the forms of narrow pulses, variable duty cycle or exponential decay rate pulses 111 which constitute the waveform output voltages submitted for delivery 125 by one or more antennae.

In an embodiment, a pulse shaping of a step recovery or drift step recovery diode is accomplished by controlling current/voltage drive waveform utilizing an arbitrary waveform generator as a means of providing sub nanosecond waveforms with a variety of asymmetric pulse shapes suited for inducing electroporation.

The pulse formations can assume square-wave, trapezoidal, delta function, step-function with exponential decay to obviate ringing, or other discrete or continuous functions. Thus, the resultant electric field is thus delivered to the target tissues as a train of ultrashort pulses 111 of picosecond, nanosecond, microsecond or longer width, selected to effect irreversible electroporation in a time-scale sufficiently shorter than thermal transport mechanisms such that the process is adiabatic. The RF excitation signal RMS power, modulation rate, pulse shape and duration, duty-cycle, and carrier frequency provide exposure time and E field magnitude for coronavirus membrane destruction. For example, the waveform, phasing, duty-cycle, power-density, and related parameters are controlled according to a computer algorithm run at microprocessor 106 for medical treatment objectives.

In an embodiment, the amplitude control is influenced by sensor feedback signals 615 received from an adaptive feedback control system 600 comprising arrays of E field capacitive probe arrays embedded within the exam table or observation platform described in connection with FIG. 8. Feedback E field voltage signals via the E field capacitive probe array are input to the system microcontroller 106 which utilizes pre stored calibration routines to augment amplitude and phase control for optimum electroporation. The microcontroller 106 responds to the sensor feedback 615 to generate control signals 125 for amplitude and phase control of leveler or attenuator element 110.

The Antenna System

An antenna system is used to provide suitable electric field transport in the near reactive field. The antenna system is designed to deliver a proper E field signature, polarization, magnitude and phase in a spatial region surrounding the body and targeting electroporation. Example polarization states can include but are not limited to: a linear polarization-state, vortex, elliptical, circular, or combinations thereof. The range of propagating frequencies includes ISM bands and suitable other non-restrictive regions where signal levels operate on a noninterference basis. Antenna system designs are multi-faceted and include but not limited to loops, arrays, monopoles and dipoles, focused antenna as well as passive components that can provide wireless radiation of pulse like signals.

In an embodiment, the radiant energy field is derived from antenna form-factors such as impulse radiating, patch, monopole, dipole or quadrupole antenna elements, volume rf coil bird cage design geometry, antenna arrays, MMICS or translating or rotating elements, or cylindrical or curvilinear enclosures, encasing or in proximity to the patient.

The antenna may be in the form-factor of a waveguide, stripline, array of waveguides or striplines, or MMIC semiconductor integrated circuit, or dielectric material. Further forms of the antenna can include a conic section cross-sectional form such as: circular, elliptical, triangular, rectangular, linear or curvilinear.

The design of the antennas may vary the dimensions to accommodate patient physiological variations of skull, thoracic or related body sections.

As signal compensation is included in E field generation, tuning of the E field generation compensates for the delivery of the radiative signal and its components, transmission lines, various nearby affects, body types, variations in targets, etc.

Figure 12:
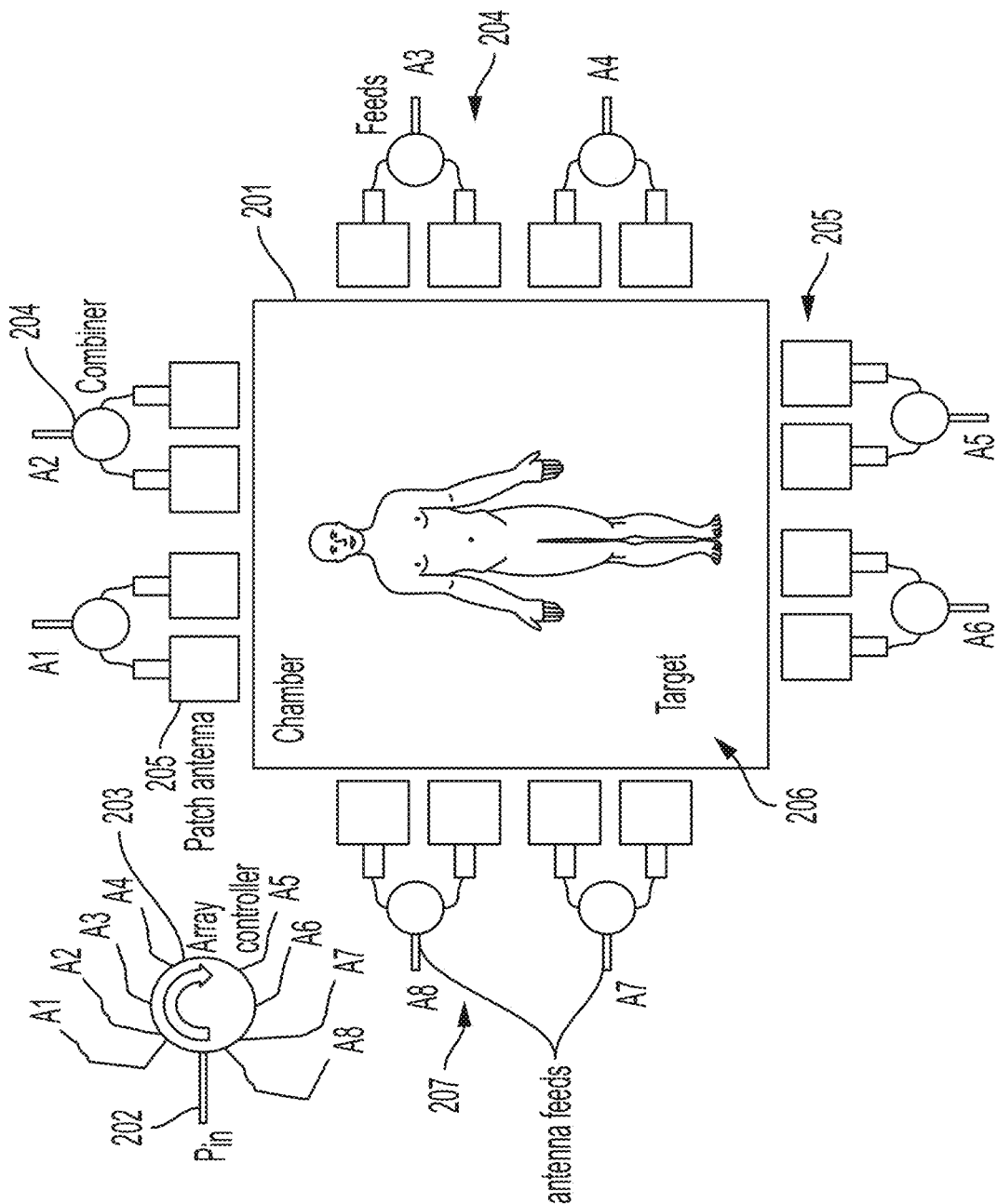
FIG. 12 is a phased-array of patch antennas under computer control for beam-forming electric fields directed to patient target zones for electroporation sterilization of Covid-19 in an example embodiment.

One embodiment utilizes patch antenna. FIG. 12 depicts a phased-array of patch antennas under computer control for beam-forming electric fields directed to patient target zones for electroporation sterilization of Covid-19. Tuning, including amplitude and phase adjustments of the E field generator, will accommodate any pulse distortion that might occur in the delivery system to the target.

Operation utilizing focused versus scanned E fields is possible via an array of patch antenna 205. The chamber and target 201 and 206 are surrounded by an array of antenna. Each patch antenna 205 in itself could be an array of antenna with gain and focus capabilities. Input to an array of patches uses printed lines, microstrip or stripline 202 and the E field excitation is distributed to the array by a combiner or array controller 203 under microprocessor control. Proper E field distribution or excitation to the target 206 requires the array controller 203 to output or to terminate excitation. The array controller includes PiN diode arrays which control amplitude as well provide phase control. This function is under control of microprocessor 106. Each patch antenna array 205 is combined via a combiner 204 and patches connected via feeders 207 ultimately routed to the E field exciter of FIG. 10. The chamber 201 houses the patient target 206 where the target may be vertical or horizontal. The RF E field voltage is applied via a power feed 202 which is input to an array controller 203 and a power combiner-splitter 204. A family of power combiners 204 feed patch antenna 205 through a systematic set of antenna feeds 207. These patch antennae can deliver a variety of E field polarizations as required by the control of the antenna feed input levels utilizing array controller 203. The array controller provides adjustable amplitude and phase control of the signal generation (output 125 of FIG. 10) applied to the antenna array, multiple arrays (elements 205 in FIG. 12). The array controller includes amplitude and phase control switches.

Another example embodiment utilizes an array of linear polarized dipoles. A single dipole 304 either vertical 305 or horizontal 307 orientation is possible. The dipole is a tuned system, however it is configurable as a broadband system if suitable impedance match and compensation is provided. The target 303 is shown in a horizontal position. The dipole(s) run the length of the target, nominally 68 inches (173 cm), and may be illuminated on top, bottom, sides or any combination as required to maintain proper E field orientation. Proper amplitude as well phase excitation is under control of an array of PiN diodes, the arrays 310 configured as amplitude control switches and switched controlled phase shift networks connected to the array controller 309, which may also contain multiple units 310. Further control is available through control of the E field generator via primary feed 308.

Examination Table

Figure 7:
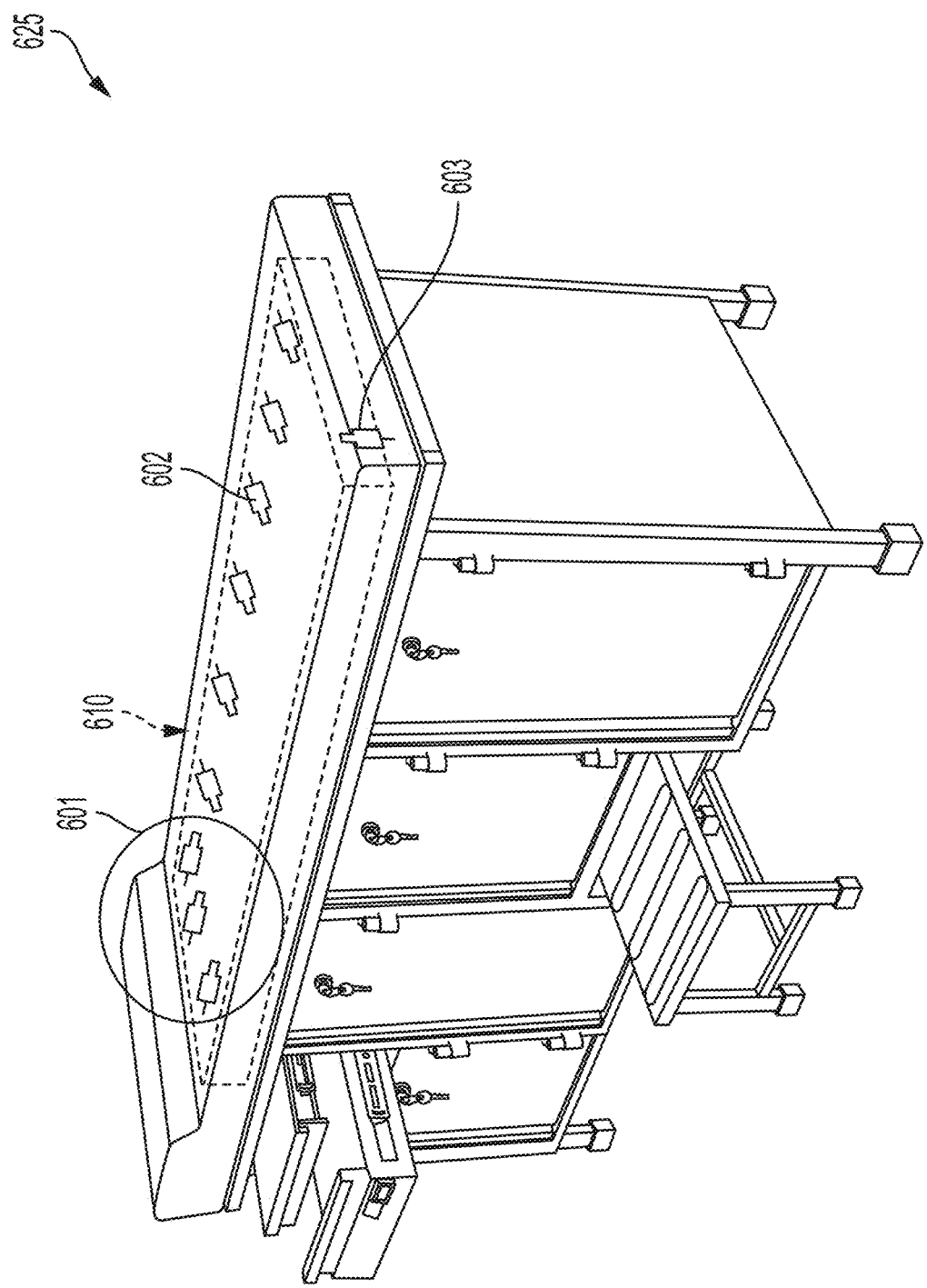
FIG. 7 depicts an examination table embedded with E field sensors used for calibration and adaptive feedback control of the antenna-based radiative electroporation therapy.

In an embodiment, a patient 303 is exposed to the polarized electric field radiation, e.g., while lying in a prone position on a table. FIG. 7 shows an example patient examination table 625 for use in the system. In an embodiment, the patient examination table includes a calibrated coordinate frame for adjustable patient support table and stepper motor positioning unit (not shown) is employed to adjust distance of patient relative to the radiant energy source(s). Below the patient table 625 in FIG. 7 is an adaptive sensor-based feedback control system including a printed laminate board 610, e.g., embedded in the table base, the board containing one or more arrays of electric (E) field sensors 602, 603 which can sense the directive E field values and provide a dosimetry gauge. In an embodiment, the sensors are configured as arrays 601 of capacitive probes 602, 603 connected to circuitry used for feedback control of the E field signal generator and antenna drives. The E field sensors embedded within the treatment table assists in body penetration depth calibration and control.

Figure 9:
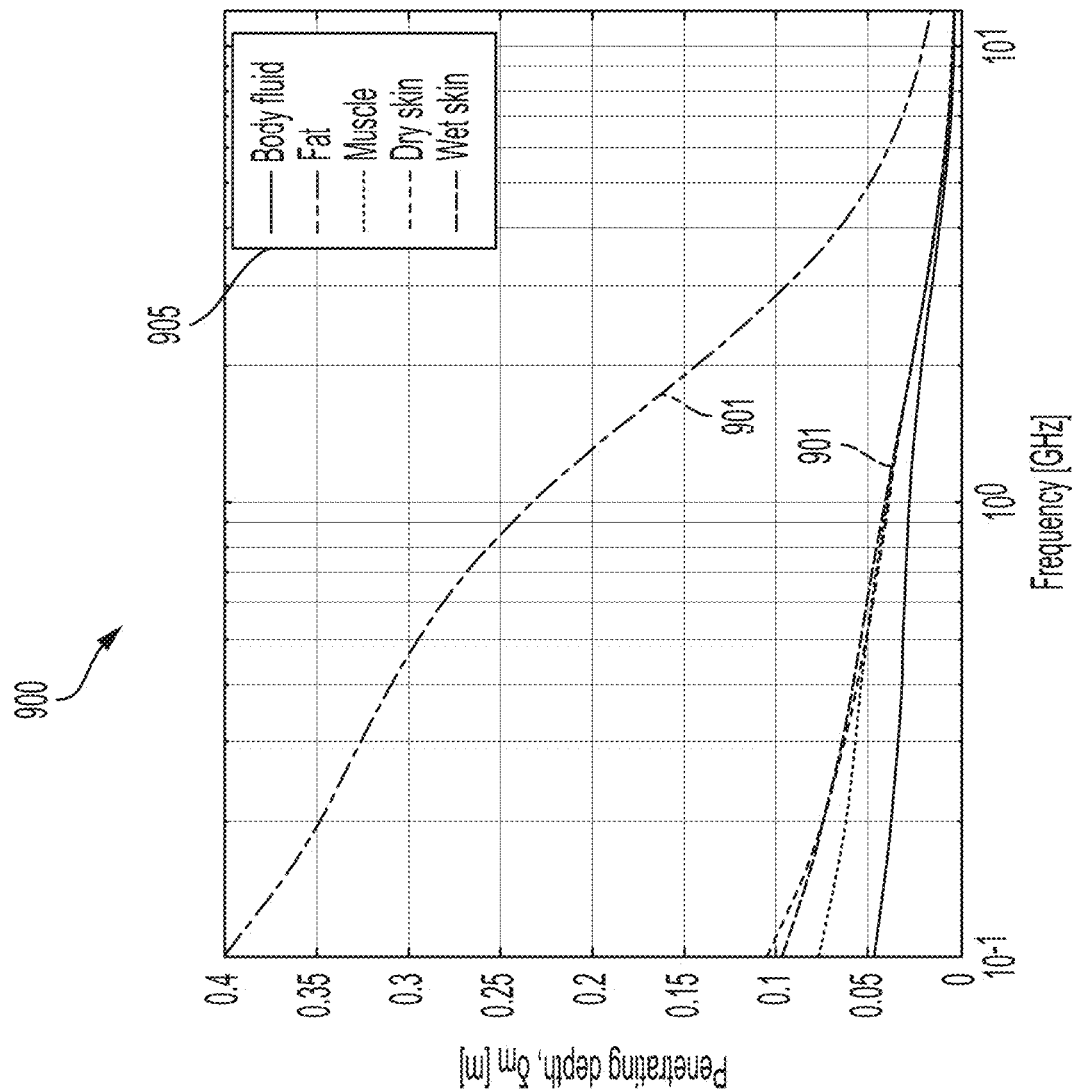
FIG. 9 is a graph of the dependence of electric field penetration depth on the dielectric properties of tissue layers in the human body.

FIG. 9 depicts a plot 900 of the penetration E field signal depths 901 within various human target tissues 905 as a function of applied E field radio frequency (RF). As carrier wavelength or radiation frequency is chosen to enable whole body penetration of the electric field consistent with the depth required to access the human tissue surfaces, plot 900 is used for system calculations to model the human body tissues subject to the exposed polarized radiation as a multilayer dielectric.

Feedback Control System

Figure 8:
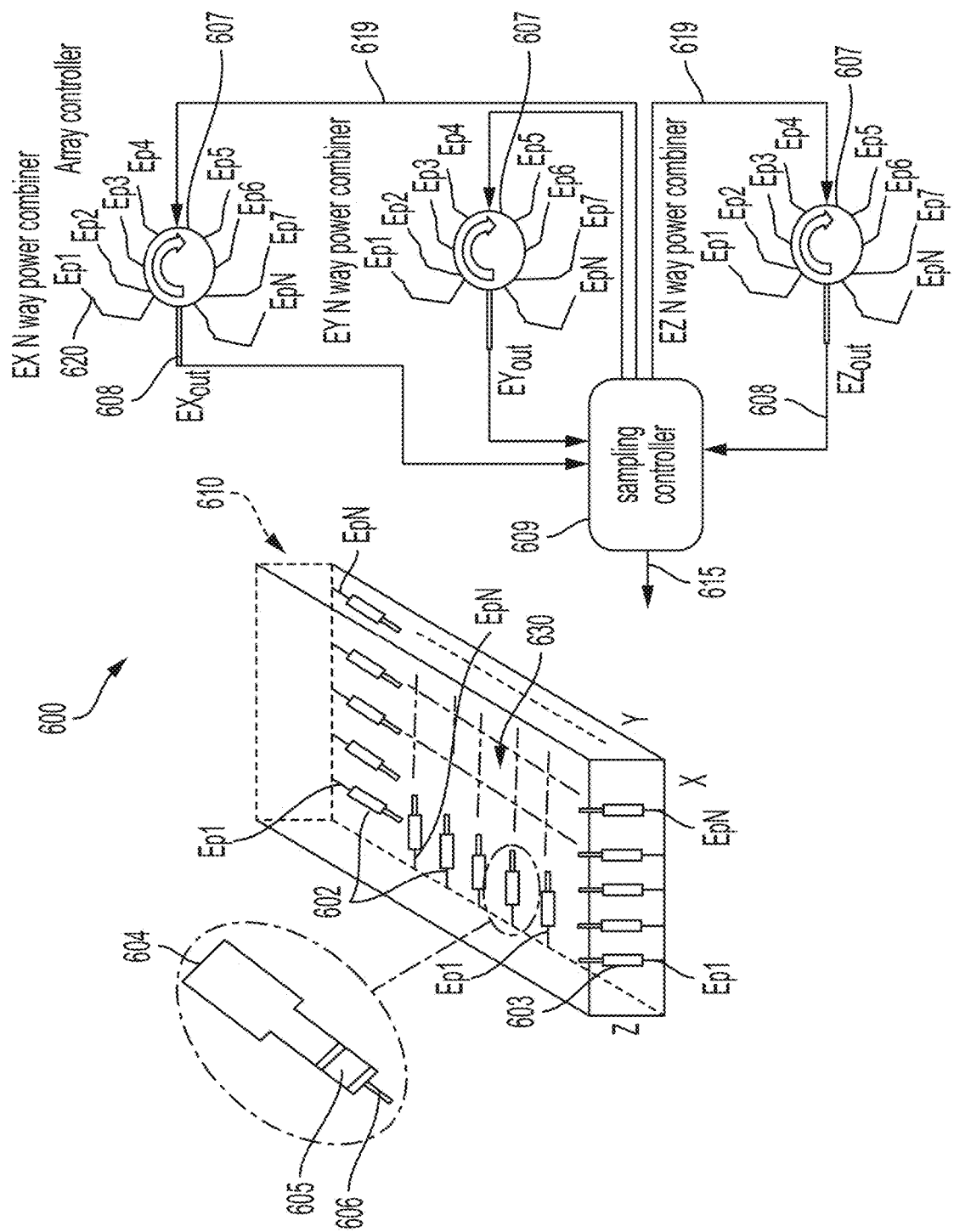
FIG. 8 is a detailed depiction of a printed laminate board embedded in the table base containing arrays of capacitive probes which can sense the directive E field values and provide a dosimetry gauge in an example embodiment.

FIG. 8 depicts the adaptive feedback electronic control system 600 in greater detail. As shown, a printed laminate board 610 embedded in a base of the exam table shown in FIG. 7 contains arrays or matrices 630 of capacitive probes 602, 603 oriented in x, y and z directions to sense the directive E field values for use in providing a dosimetry gauge. As shown, a plurality of capacitive E field sensing probes 602 making up a probe array is oriented along respective x-axis and y-axis directions, i.e., forming x-axis plane and y-axis plane sensor probe arrays. A plurality of capacitive E field sensing probes 603 making up a probe array is further oriented along a z-axis plane. Each of the probes 602, 603 of the arrays along x-, y- and z-axis planes sense radiated electric field components in the respective x, y, z axis direction and each array of a respective plane includes a plurality, e.g., 'N' probes. Each array of E field sensors is placed within the treatment table and assists in body penetration depth calibration and control. The arrays of E-field probes arrayed in proximity to the target patient and provide capacitive probe outputs, e.g., Ep1 through EpN, each connected to control circuitry for applying functional computer control to enable adaptive beam-forming array elements to adapt to system parameters related to patient variables. Such an arrangement of arrays of 'N' capacitive probes 602, 603 and respective output signals Ep1 through EpN can sense the directive E field values in each the X, Y and Z directions for further use in gauging E field polarization, and in addition, providing feedback for control of the E field generator. That is, the patient examination table or bed provided with an array of E field sensors provides adaptive feedback control of antenna positions, orientation, target alignment, and control of signal emission levels for assuring each antenna element will not exceed SAR limits.

In an embodiment, as shown in FIG. 8, each probe sensor 604 consists of a microstrip line, a film capacitor 605 and a probe sensor tip 606. However, other types of E sensing probes can be implemented.

In an embodiment, as shown in FIG. 8, the control system 600 includes circuitry for applying functional computer control to enable adaptive beam-forming array elements to adapt to system parameters related to patient variables. The circuitry includes N-way power combiners 607, each N-way power combiner 607 corresponding to a respective E field component direction. Each respective power combiner includes inputs 625 from respective Ex, Ey and Ez inputs received from corresponding array of N probes, Ep1 through EpN from a respective plane orientation. Under control of sampling controller 609, a sampling signal 619 is generated to configure switches for sampling a respective sensed probe output values Ep1, . . . , EpN in round robin fashion from each respective combiner 607. Each of the E field power combiners 607 output sampled feedback voltages 608, e.g., Ex_out, Ey_out, Ez_out, that are provided back to the micro controller 106 via a sample controller 609. The sample controller device 609 provides sensor feedback and control is provided by a calibration and run time routine to ideally control electroporation. In an embodiment, the run time routine uses capacitive probe sensor array outputs to generate a map of electric field values in the set of planes of the patient target tissues for algorithmic control of treatments. This routine is provided by and implemented at the main microcontroller 106.

The Power Generator and Delivery System

Requirement for electroporation is nominally a peak field of 100 kV/m, however may range between 100 kV/m and 150 kV/m for electroporation of Covid virus. Other ranges are possible depending upon the biological target and other variables, and the E field generator system accommodates a wide range in settings. The pulse wave RMS E field value requires a magnitude based on the wave duty cycle and is given by:

$$E_{RMS} = E_{peak}\left(\sqrt{\frac{\tau}{T}}\right)$$

If the applied pulse frequency is 40.6 MHz, then the T value is 24.6 ns and a suitable pulse width, τ is 30 ps. The decaying exponential pulse is favorable to electroporation and minimizes the potential for fall time pulse ringing. The relation between peak and RMS is given by:

$$E_{RMS} = \frac{E_{peak}}{\sqrt{2k}}$$

where the value of k is the decay time in relation to the pulse duration and can be a 1000 times shorter than the pulse period. This reduces the required RMS value of the E field.

As shown in FIG. 11 depicting the chamber antenna drive circuitry 400 receiving output pulses 111 generated from the electric field generation circuit 150, accommodation of the radiant pulse E field requires power amplification, impedance matching between the E Field generator and amplifier and antenna(s). In addition, compensation is required to minimize pulse distortion. Input impedance matching to the high power amplifier or HPA 402 is provided between the amplifier input and the E field generator via impedance matching unit 401. The HPA requires output matching and phase compensation 403 and 404 prior to interface to the radiant array. The impedance interface to the antenna array is via antenna matching 405. These networks are either low, high or bandpass as required to minimize pulse distortion. The HPA 402 will operate at a suitable power level to achieve the required E field and this value will depend on system attributes such as antenna type 406, gain, loss, operating frequency and pulse type of input pulse/pulse train 111. Example design values are for an HPA at a power level of 150 watts.

In an example embodiment, HPA 402 is a 150 W power amplifier configured to provide a composite E field of 3 kV/m RMS. The resultant peak field transmitted by dipole antenna 406 is $E_{peak}$ where $E_{peak}=E_{RMS}/\sqrt{tau/T}$ as provided by a rectangle pulse 111, where tau is 22.5 pS and T is approximately 1/40 MHz or 25 ns thereby delivering an $E_{peak}$ of about $$3000 \text{ V/m} \Big/ \sqrt{\frac{22 \times 10 - 12}{25 \times 10 - 9}} \approx 100 \text{ kV/meter.}$$

Other waveforms and associated duty cycles will provide different requirements on the desired power.

Example E Field Distribution

To achieve IRE (irreversible electroporation of threshold for virion membrane), in vivo, and without Joule heating or heat transfer, an external electric field of specific critical electric field strength of no less than 0.1 MV/m or 0.15 MV/m is delivered by RF antenna to target tissue surfaces where virions attach to ACE 2 and other receptors.

In embodiments, electric field magnitudes for electroporation can span an interval greater than the electroporation threshold and less than the regulatory safety standard SAR values. In embodiments, a fixed "guard rail" limit below the SAR safety_limit can be built into the computations to ensure patient avoidance of excessive electric field exposure. Characteristic time-constants to achieve electroporation begin below 1 nsec. Electric field vectors operate on the virus's membrane surface via the Coulomb force on the positive hydrophylic charges of polymers comprising a matrix of electric dipoles. The collective resultant forces comprise the Maxwell stress tensor.

FIG. 6A depicts x-axis and y-axis direction components and FIG. 6B depicts z-axis direction components of an electric field spatial distribution 501 in a coordinate system relative to a target patient undergoing antenna-based radiative electroporation therapy 503. Using an example thin dipole array 502 such as shown in FIG. 6B, there is achieved an exemplary E field spatial distribution 501 shown in FIGS. 6A and 6B. In the example depicted, a patient target 550 is located on a platform in the XY plane with the thin wire dipole 502 overhead. In an embodiment, the E fields are generated from a thin wire dipole antenna, e.g., of 68 inches length, located above a plane with conductivity and dielectric constant of 0.014 S/M and 80. As shown in FIGS. 6A and 6B, applied electric fields are provided as a distribution 501 in the XY plane. For example, the E field distributions, i.e., E field strength (V/m vs. distance in respective x, y and z directions) are: Ex 501A, Ey 501B and Ez 501C displayed in the XY plane as originating from the respective x, y and z direction planes 501. The composite peak field is provided by the square root of the sum of the squares of each of the E field values and reaches a peak value of 100 kV/m. The E field is projected 503 to expose the relevant peak E field to the target. In an example, a goal of the E field composite is to deliver 3.5 kV/m RMS to the target patient and is determined based on a pulse width of 30 ps and a period of 24.6 ns.

In an embodiment, antenna elements are placed above and below the patient plane for superposition adaptations to generate controlled electric field intensity or vector patterns for uniform electric fields or adaptive electric field patterns.

Calibration and Adaptive Feedback Control

FIG. 13 depicts an example embodiment of an antenna near field alignment algorithm 700 for calibration and adaptive feedback control. In particular, the method 700 of FIG. 13 uses the control system 600 of FIG. 8 and the E field sensors embedded within the treatment table to evaluate and assist in body penetration depth calibration and control. The calibration and use of E-field probes arrayed in proximity to the target patient are ultimately used to apply functional computer control to enable adaptive beam-forming array elements to adapt to system parameters related to target patient variables. For example, the array of E field (capacitive probe) sensors in the patient exam table coupled with adaptive control circuitry provides adaptive feedback control of antenna positions, orientation, target alignment, and, control of signal emission levels for assuring each antenna element will not exceed SAR limits.

In FIG. 13, using the microcontroller 106, at step 702, an initial process configures the E field RF generator and arbitrary waveform (modulator) generator, high power amplifiers, etc. to establish initial pulse waveforms and exponential decay of pulses for transmission via the antenna system (e.g., patch or dipoles) as polarized E field radiated signals. At 702, there is nothing placed on the examination table or in the chamber. Then, at 704, the plurality of capacitive E field sensing probes 602 making up the probe arrays of control system 600 are used to obtain E field measurements in each direction for calibration, and at 712, baseline Ex, Ey and Ez values are obtained for each of the sensing probes and a baseline data sets for Ex, Ey and Ez excitation levels for the target spatial region, e.g., examination table, are generated. These values are inspected at 715 and a calibration table is built to contain the raw E field values at 720. Continuing to 718, a determination is made to ensure all values are obtained for the target spatial region covered by the sensor probe arrays are within expected ranges as programmed. For example, it can be determined at 718 whether there exists any dead spots or no/excessive voltage(s) sensor probe values measured at a location can indicate a bad connection, a probe misalignment, or an additive or destructive interference, a faulty or misaligned antenna etc. If such issues are determined that require a fix, the process returns to 704 to correct the probe(s), antenna and/or re-program the RF excitation/waveform. For example, this may include a physical inspection of the sensor probe arrays, replacing probes or re-orienting probes, fixing antenna orientations, antenna cable interconnect losses, etc. Then, at 712, new E field measurement values from the sensor probes are obtained and a raw values array table is built at 720 that provides a mapping of electric field values in the set of planes for ultimate use in algorithmic control of treatments. The loop comprising steps 704, 712, 715 and 718 are repeated until it is determined that sensed antenna-radiated pulses power level and waveform power are within expected ranges, i.e., all raw baseline sensor E field values are within expected ranges at every point of the spatial region to provide an adequate mapping. Once all issues are addressed, the system updates the raw E field values of the sensor array table built at 720 to ensure a correct image, e.g., a correct mapping of the Ex, Ey and Ez pattern (e.g., a uniform pattern of E field vectors) is obtained, and the process proceeds to step out of 718.

At 718 output, once the generated raw E field values are successfully determined, the process proceeds to 725, FIG. 13, where a phantom model (e.g., a dielectric model of the target patient) is placed on the examination table that models the physical attributes of a subject to be scanned. Then, at 725, new measurements are obtained by the E field probe sensor arrays using the current RF excitation and pulsed waveform settings.

Continuing to 728, a comparison step is performed to obtain the difference in sensed E field level values between the raw E field sensor values with no phantom present and the E field sensor values obtained with the phantom model in place on the table. Based on the differences, at 730, the system generates an antenna array error table which indicates a manner for which the microprocessor 106 can respond to provide any E field magnitude and/or polarization or phase adjustments delivered by the antennae to within the fixed guard rail below the SAR value at each measured point at the table. That is, based on the differences, the microprocessor at 735 can use the values to determine whether any refinement/adjustment of the operating parameters (e.g., RF excitation, waveform amplitude, phasing, duty-cycle, etc., is necessary in order to provide a uniform E field vector at the desired polarization. Then at 740, the system generates a corrected E field array table with near field Ex_out, Ey_out, Ez_out data set values sufficient to ensure the generation of the Maxwell stress tensor for electroporation is achievable adiabatically within the SAR safety limit of the signals for delivery by each antenna or their ensemble.

In an alternate embodiment, an initialization method of system calibration can be based on using opposing side antennas to serve as source and a test for fixing antenna polarization state and E field intensity. To initialize the apparatus of the system, antenna elements on opposing sides of the chamber 301 for the dipole element, and for the patch element, are each excited as a source and a test antenna. When the polarization state of these opposing antenna are matched, the signal current is maximized, and a table of values may be stored for lookup. This method of calibration assures real-time measurements confirm operations parameters are properly set to the algorithmic treatment conditions.

Figure 14:
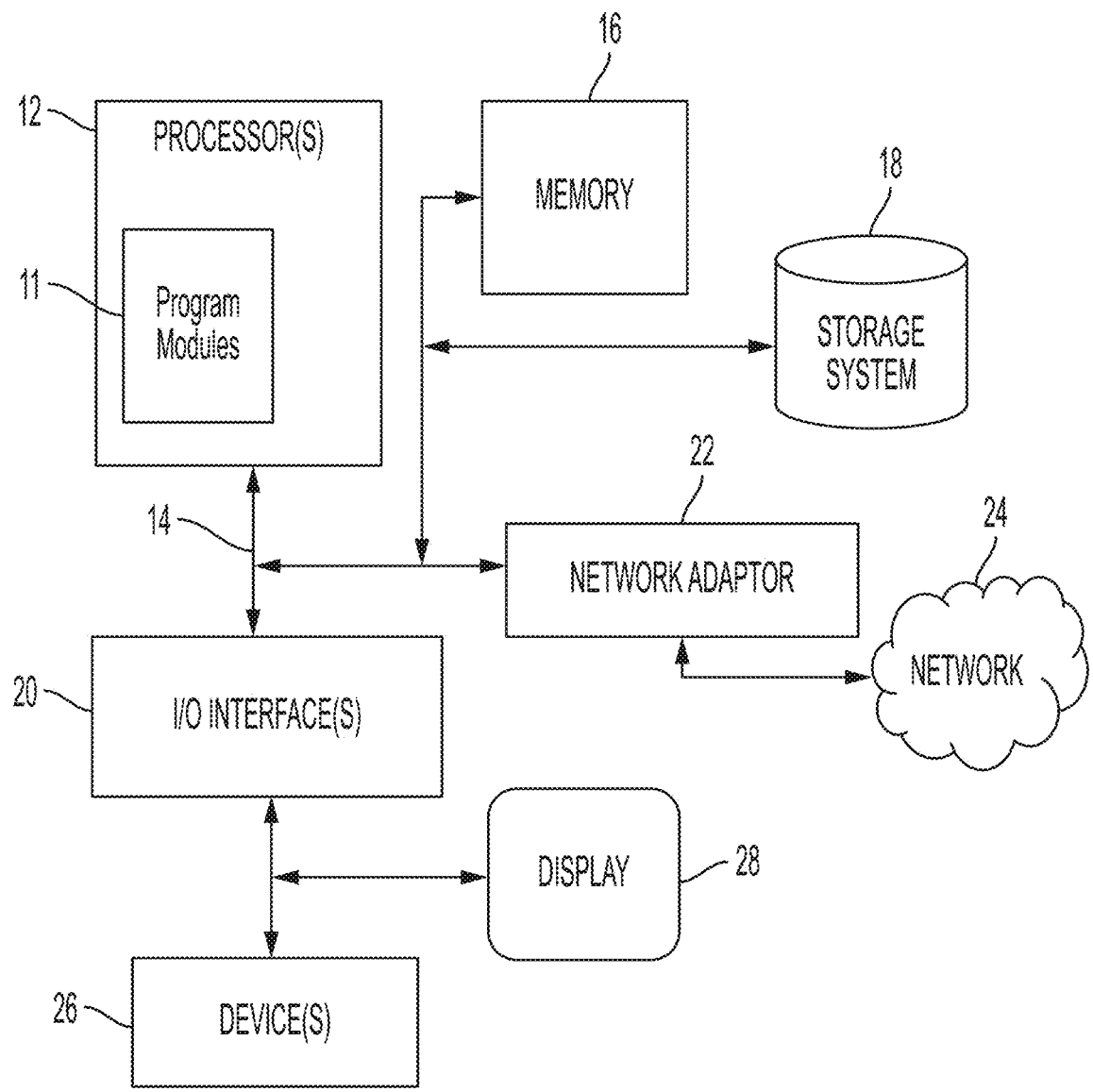
FIG. 14 illustrates a schematic of an example computer or processing system that may implement methods for calibrating a polarized electric field system according to embodiments herein.

FIG. 14 illustrates an example computing system that is used in accordance with the present invention. It is to be understood that the computer system depicted is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 14 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Figure 13:
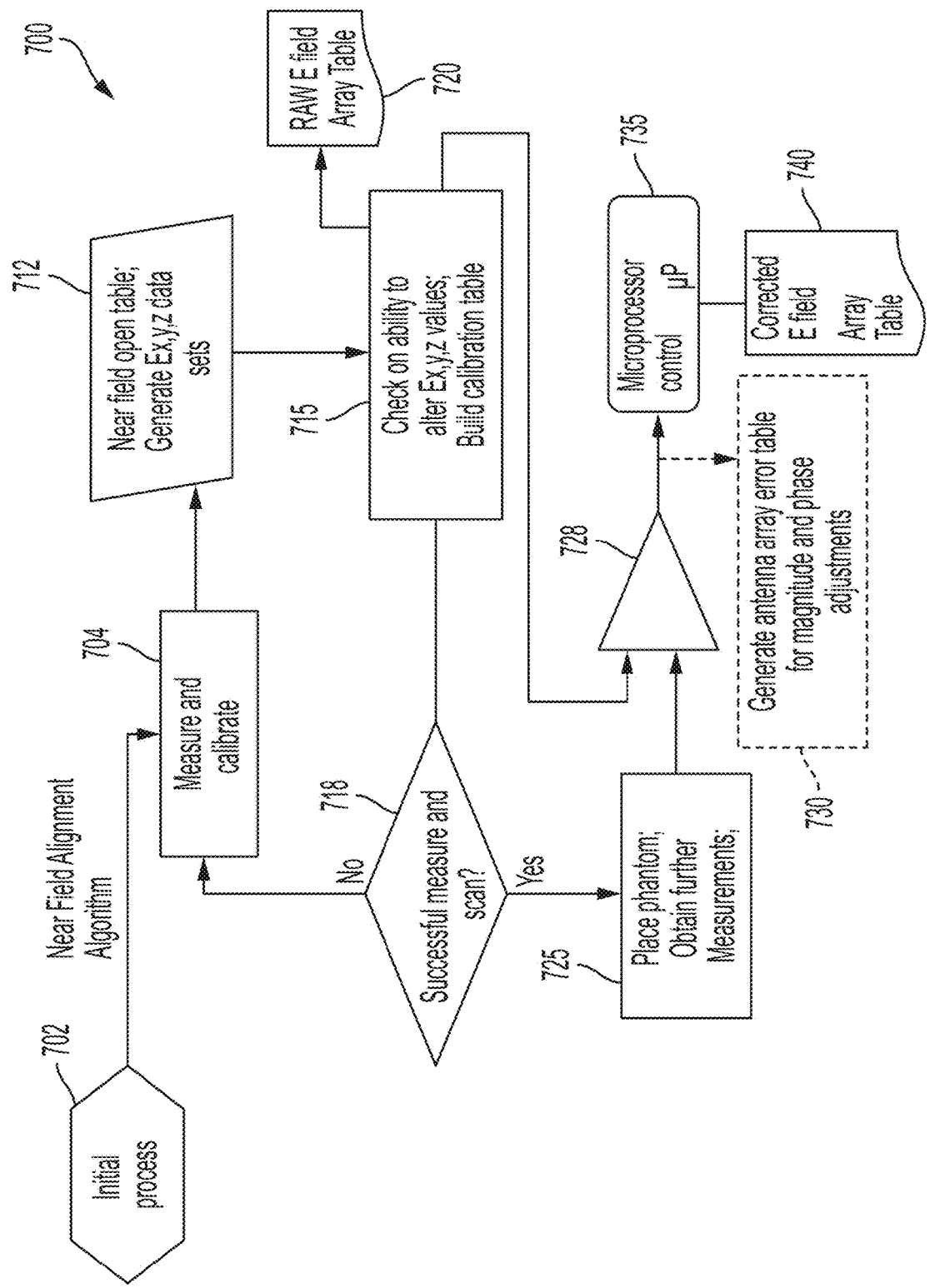
FIG. 13 depicts an exemplary alignment method for aligning polarized radiating electrical signals in the near field in an embodiment.

In some embodiments, the computer system may be described in the general context of computer system executable instructions, embodied as program modules stored in memory 16, being executed by the computer system. Generally, program modules may include routines, programs, objects, components, logic, data structures, and so on that perform particular tasks and/or implement particular input data and/or data types in accordance with the present invention (see e.g., FIGS. 10, 13).

The components of the computer system may include, but are not limited to, one or more processors or processing units 12, a memory 16, and a bus 14 that operably couples various system components, including memory 16 to processor 12. In some embodiments, the processor 12 may execute one or more modules 11 that are loaded from memory 16, where the program module(s) embody software (program instructions) that cause the processor to perform one or more method embodiments of the present invention. In some embodiments, module 11 may be programmed into the integrated circuits of the processor 12, loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

Memory 16 (sometimes referred to as system memory) can include computer readable media in the form of volatile memory, such as random access memory (RAM), cache memory an/or other forms. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A non-invasive radiative electroporation system for in vivo selective destruction or sterilization of biological targets within a patient, the system comprising: a radio frequency signal generator generating polarized radiant energy signals at one or more radio frequency antennas, each antenna located in accordance with a three-dimensional reference frame coordinate system proximate the patient and having a geometry for delivering specific radiative near-field polarized radiant energy at a selected field intensity level to tissues of the patient having said biological targets; an electronic circuit configured to modulate said polarized radiant energy signals according to a configured waveform and exposure time for delivery of said polarized radiant energy signals to said biological targets; a patient support table adapted for adjusting positioning of the patient relative to the one or more radio frequency antennas, in accordance with the three-dimensional reference frame coordinate system; one or more processors coupled to a memory storage for storing computer readable instructions, one processor of said one or more processors adapted to run said computer-readable instructions to configure said electronic circuit to adjust operating radiant energy parameters for controlling said waveform and exposure time; and an adaptive feedback control system comprising a plurality of electric field sensors embedded within or disposed below said patient support table configured to sense in three-dimensions said polarized radiant energy signals delivered to said patient tissues, provide sensor values for generating a map of electric field values in said three dimensions and generate associated feedback signals representing the map of electric field values in said three dimensions, said one processor of said one or more processors configured to use said feedback signals to adaptively control antenna positions, antenna orientation, alignment of biological targets, and control signal emission levels for constraining said delivered polarized radiant energy signals to within a specified electrical field intensity level safety limit.

2. The electroporation system as claimed in claim 1, wherein the polarized radiant energy signals comprise an electric-field of a critical intensity sufficient to result in irreversible electroporation of the biological targets, the biological target comprising one or more of: a carcinoma, a virus, a coronavirus, a bacteria, cardiac or cardiovascular tissues, a vascular system, a neuron network, and a cancer tumor, said electric-field of a critical field intensity further sufficient to result in destroying a virus lipid bilayer membrane and annihilating intra-membrane replicative organelles of said biological target.

3. The electroporation system as claimed in claim 2, wherein the radio frequency signal generator generates an RF excitation signal, wherein an RMS power, a modulation rate, a pulse shape and duration, a duty-cycle, and a carrier frequency are configured to control an exposure time and E field magnitude for destroying said biological targets.

4. The electroporation system as claimed in claim 2, wherein the radio frequency signal generator is adjustable to configure one or more of: an amplitude, frequency, a phase shift, a polarization state, a beam-form, or a state of quadrature excitation of the polarized radiant energy signals in a manner sufficient to achieve the critical intensity and optimum polarization of said electric-field.

5. The electroporation system as claimed in claim 4, wherein said electric field is delivered as a pulse or time-series of pulses, said electronic circuit comprising an arbitrary waveform generator for adjusting one or more operating radiant energy parameters selected from the group comprising: a pulse shape, a pulse width, a pulse height, a duty-cycle, an amplitude or frequency modulation, a power-density, or a continuous wave, said pulse or time-series of pulses of a time-scale duration such that said delivery of said polarized radiant energy signals is adiabatic.

6. The electroporation system as claimed in claim 5, wherein the pulse shape comprises one of: a square-wave, a trapezoidal wave, a delta function, or a step-function with exponential decay.

7. The electroporation system as claimed in claim 5, wherein said electronic circuit further comprises:
a step recovery diode or drift step recovery diode generator for shaping said pulse(s) responsive to a programmed current/voltage drive waveform.

8. The electroporation apparatus system as claimed in claim 7, wherein said arbitrary waveform generator is programmed to adjust said current/voltage drive waveform to achieve a sub-nanosecond pulse shape suited for inducing said irreversible electroporation using said step recovery diode or drift step recovery diode, said pulse shape comprising one of: a square, a trapezoidal, a delta function, or a step-function with exponential decay.

9. The electroporation system as claimed in claim 7, wherein said one or more radio frequency antennas have a cross-sectional form defining a circular, elliptical, triangular, rectangular or curvilinear conic section.

10. The electroporation system as claimed in claim 9, wherein said one or more radio frequency antennas comprise one or more of: translating elements, rotating elements, a cylindrical enclosure, a curvilinear enclosure, or an encasing.

11. The electroporation system as claimed in claim 9, wherein the one or more antennas comprise a dipole antenna having discrete segments or sections adaptable for controlling generation of a radiation pattern.

12. The electroporation system as claimed in claim 11, wherein the dipole antenna is rotated for generating controlled emission patterns and polarization states of the electric field.

13. The electroporation system as claimed in claim 9, wherein said one or more radio frequency antennas are positioned at locations above or below a plane of the patient support table, or both above and below the plane of the patient support table to superimpose radiant energy fields for controlling an electric field intensity or a field vector pattern to create a uniform electric field or desired electric field pattern.

14. The electroporation system as claimed in claim 2, wherein the one processor of said one or more processors is configured to respond to said associated feedback signals to adjust said operating radiant energy parameters to prevent an intensity level of said electrical field from exceeding a fixed level below a specified absorption rate (SAR) limit.

15. The electroporation system as claimed in claim 14, wherein the plurality of electric field sensors is configured as one or more 3-dimensional arrays, the generated map of electric field values in said three dimensions comprising a map of electric field values in a set of planes of the biological targets within the patient.

16. The electroporation system as claimed in claim 15, wherein said one processor of said one or more processors is further configured to receive, as feedback signals, said map of electric field values to determine a patient's body penetration depth of said polarized radiant energy signals, and in response, calibrate the system to deliver said polarized radiant energy signals within the SAR limit.

17. The electroporation system as claimed in claim 1, wherein a polarization-state of said radiant energy signals comprises: a linear polarization, a vortex polarization, an ellipsoidal polarization, a circular polarization, or combinations thereof.

18. The electroporation system as claimed in claim 1, wherein the one or more radio frequency antennas are of a form-factor comprising: a waveguide, a stripline, an array of waveguides or striplines, a monolithic microwave semiconductor integrated circuit (MMIC), a dielectric material, an impulse radiating, a patch, a monopole, a dipole or quadrupole or arrays thereof, said dipole or quadrupole of a dimension configured to accommodate patient physiological variations of skull, thoracic or related body sections.

19. The electroporation system as claimed in claim 18, wherein said one processor of said one or more processors configures said dipole antenna or array of dipole antennas to scan in a lateral or longitudinal direction across said patient when positioned on said patient support table, or scan via a rotation to provide for whole body coverage of said patient.

20. The electroporation system as claimed in claim 18, wherein the one processor of said one or more processors is configured to respond to said associated feedback signals to adjust said operating radiant energy parameters according to physical patient variables, a medical treatment objective, or both physical patient variables and medical treatment objectives.

* * * * *